United States Patent [19]

Barnard et al.

[11] Patent Number: 5,852,126
[45] Date of Patent: Dec. 22, 1998

[54] POLYMERISABLE COMPOSITION AND THE USE THEREOF

[75] Inventors: Steven Barnard, Wellesley Hills, Mass.; Marizel Rouilly, Gipf-Oberfrick, Switzerland

[73] Assignee: Novartis AG, Basel, Switzerland

[21] Appl. No.: 737,029

[22] PCT Filed: Mar. 27, 1995

[86] PCT No.: PCT/IB95/00301

§ 371 Date: Oct. 30, 1996

§ 102(e) Date: Oct. 30, 1996

[87] PCT Pub. No.: WO95/29959

PCT Pub. Date: Nov. 9, 1995

[30] Foreign Application Priority Data

May 2, 1994 [CH] Switzerland ............... 1360/94
Apr. 11, 1995 [CH] Switzerland ............... 1068/95

[51] Int. Cl.[6] ............... C08F 214/18; C08F 291/00; C09B 69/10; B32B 17/10
[52] U.S. Cl. ............... 525/326.3; 525/326.1; 8/647; 428/441; 435/808
[58] Field of Search ............... 525/326.3, 326.1; 8/647; 428/441; 435/808

[56] References Cited

U.S. PATENT DOCUMENTS

| | | | |
|---|---|---|---|
| 3,351,603 | 11/1967 | Chen et al. | 260/31.2 |
| 4,326,008 | 4/1982 | Rembaum | 428/403 |
| 4,999,456 | 3/1991 | Fong | 564/207 |
| 5,043,406 | 8/1991 | Fong | 526/304 |
| 5,409,504 | 4/1995 | Fritzsche | 8/444 |

FOREIGN PATENT DOCUMENTS

| | | |
|---|---|---|
| 60935 | 9/1982 | European Pat. Off. . |
| 97012 | 12/1983 | European Pat. Off. . |
| 88/05533 | 7/1988 | WIPO . |
| 94/28786 | 12/1994 | WIPO . |

OTHER PUBLICATIONS

Patent Abstract of Japan 61 145208, vol. 10, No. 339.
Chemical Abstracts, vol. 81, 153066 (1974).
Derwent Abstracts, of AL.

*Primary Examiner*—Joseph L. Schofer
*Assistant Examiner*—Wu C. Cheng
*Attorney, Agent, or Firm*—William K. Wissing

[57] ABSTRACT

The invention is directed to compositions containing at least one olefinic monomer, at least one polymer prepared form an olefinic monomer, an indicator dye to the basic structure of which an olefinic polymerisable group is covalently bonded directly or via a bridge group, at least one diolefinic cross-linking agent, and an effective amount of a polymerisation initiator; to polymerisates of the compositions, the polymerisates being in the form of interpenetrating networks; to membranes and unsupported films prepared from the polymerisates; to carrier materials coated with the compositions and polymerisates; to optical sensors prepared from the polymerisates; and to methods of determining ions and/or gases in solutions and/or blood.

43 Claims, No Drawings

POLYMERISABLE COMPOSITION AND THE USE THEREOF

The present invention relates to a composition comprising (a) at least one olefinic monomer (A), (b) a polymer of an olefinic monomer, (c) an indicator dye to the basic structure of which an olefinic polymerisable group is covalently bonded directly or via a bridge group, (d) at least one at least diolefinic cross-linking agent, and (e) at least one polymerisation initiator; to polymers from that composition; to a material coated with the polymer; and to the use thereof.

WO 88/05533 describes sensor membranes that can be copolymerisates of vinylically substituted dye indicators and acrylamides or methacrylamides. The copolymerisates are produced directly on an optical carrier material, for example a glass fibre, for example by dipping a glass fibre into the mixture of monomers, removing the glass fibre and then polymerising the layer. The surface of the glass fibre is functionalised beforehand with acrylamides, so that the polymer is likewise covalently bonded to the surface. Membranes on which a dye indicator has been immobilised are obtained from which it is virtually impossible for the polymer-bonded dye to be washed out. A disadvantage of the described membranes is especially that their layer thicknesses are dependent upon the composition chosen/the viscosity thereof and cannot be controlled in a targeted manner, which has a direct adverse effect on the response times and sensitivities. Usable membranes are therefore obtainable only by chance depending upon the consistency of the monomers chosen.

WO 93/07483 describes sensors for indicating pH value in which the indicator dye is covalently bonded to the hydrophilic polymer membrane in order to prevent it from being washed out through use. The immobilisation is carried out by subsequent treatment of the membrane with a dissolved dye indicator containing functional groups that are capable of reacting with functional groups of the polymer membrane. Furthermore, only certain pre-prepared polymers can be used for a membrane, the mechanical and physical properties of which cannot be selectively adapted to the intended use. The manufacturing process is by its nature associated with a high degree of variation in product quality (for example in the content of dye indicator) which renders continuous production and application in standard systems difficult or impossible.

Analytica Chimica Acta, 276 (1993), 347–352 discloses an electrochemical sensor which contains on a measuring electrode an ion-sensitive membrane which consists of a cross-linked methacrylate polymer obtained in the presence of polyvinylpyrrolidone. There is no mention of the properties for an optical ion sensor and for this measuring method immobilisation with a dye indicator is not required and is not described.

It has now been found, surprisingly, that polymers of hydrophilic olefinic monomers (A) containing a homo- or co-polymer of the same monomer (A) or of hydrophilic monomer(s) (B) different from (A) and an olefinically substituted dye indicator are excellently suitable as membranes for optical sensors for the determination of ions or gases, for example oxygen or carbon dioxide. The membranes have excellent mechanical strength and the dye indicator is covalently bonded to the polymer spine and therefore cannot be washed out by the measuring solution, which in total ensures a long usable life. The membranes exhibit the necessary optical transparency as a result of an unexpected homogeneous consistency. The desired degree of hydrophilicity can be adjusted in a targeted manner so that, especially for optical pH detection, the pH measuring range can be predetermined by the choice and amount of the hydrophilic monomers and polymers. A further great advantage is that economical production processes, for example spin casting processes, can be used for the coating of the carrier materials, since the viscosity of the polymerisable composition can be set and adapted to the process technology by the choice and amount of the hydrophilic polymer. In addition, ecologically favourable manufacturing processes for mass production are possible, since aqueous coating solutions can be used and the polymerisation can be carried out directly on the carrier material. There is thereby obtained a high degree of production conformity especially with regard to the layer thicknesses, even in the case of very thin layers, so that standard calibration is generally adequate and further calibration is unnecessary if the sensors should be replaced. Furthermore, it is possible to produce very thin but at the same time uniform layers. The polymerisable compositions have adequate storage stability and can be marketed as such. The polymerisates from the compositions surprisingly form a network in which the polymer molecules of the monomers (A) are embedded or, as it were, penetrate the network. It is surprising that no segregation is observed but that, on the contrary, there is uniform distribution of the polymer molecules, so that the polymerisate is a homogeneous material.

The invention relates to a composition comprising (a) at least one olefinic monomer (A), (b) at least one polymer of at least one olefinic monomer, (c) an indicator dye to the basic structure of which an olefinic polymerisable group is covalently bonded directly or via a bridge group, (d) at least one at least diolefinic cross-linking agent, and (e) an effective amount of a polymerisation initiator.

The desired properties of the membrane can be varied and set within a wide range by the choice of the monomers (A) and the component (b) polymers and the combination thereof. For the optical detection of ions or for pH measurements in aqueous media, hydrophilic membranes are generally preferred. The hydrophilic character can be set by the choice and amount of hydrophilic monomers (A), optionally in admixture with hydrophobic monomers, and the quantity ratios thereof, and by the choice and amount of the component (b) polymer and the hydrophilicity thereof which is determined by the content of hydrophilic and/or hydrophobic monomers. In the optical detection of gases in media which may be liquid, for example blood, preference is generally given to hydrophobic membranes that can be obtained and adjusted as above but using hydrophobic monomers (A) and component (b) polymers. Hydrophilic and hydrophobic monomers and polymers may accordingly be combined as desired with other hydrophilic and/or hydrophobic monomers and polymers in order to obtain the desired properties.

"Hydrophilic" may indicate a solubility in water of at least 1% by weight, preferably at least 10% by weight, especially at least 20% by weight, more especially at least 40% by weight and very especially at least 50% by weight, the percentages being based on the solution.

The component (b) polymer may comprise at least one monomer identical to (A), at least one monomer (B) that is different from (A), or a mixture of such monomers. In a preferred form the component (b) polymer is composed predominantly, and especially solely, of monomer (A).

The hydrophilic olefinic monomers (A) and/or (B) may be present in an amount of from 5 to 95% by weight, preferably from 10 to 90% by weight, especially from 10 to 80% by weight and more especially from 20 to 70% by weight, based on the composition. The same applies to hydrophobic monomers or mixtures of hydrophobic and hydrophilic monomers.

The hydrophilic component b) homo- or co-polymers may be present in an amount of from 95 to 5% by weight, preferably from 90 to 10% by weight, especially from 90 to 20% by weight and more especially from 80 to 30% by weight, based on the composition. The same applies to hydrophobic polymers or polymers composed of mixtures of hydrophobic and hydrophilic monomers.

The indicator dye may be present in an amount of from 0.01 to 10% by weight, preferably from 0.1 to 5% by weight and especially from 0.5 to 3% by weight.

The polymerisation initiator may be present in an amount of from 0.1 to 20% by weight, preferably from 0.5 to 10% by weight and especially from 1 to 8% by weight.

The composition according to the invention comprises a cross-linking agent, for example in an amount of from 0.1 to 30% by weight, preferably from 0.5 to 20% by weight, especially from 0.5 to 10% by weight and more especially from 0.5 to 5% by weight.

The numerical values of the percentages by weight always add up to 100% by weight.

The monomers (A) or (B) are preferably selected from the group of olefins substituted by at least one hydrophilic radical. The hydrophilic radical(s) is/are selected especially, for example, from the group consisting of pyrrolidonyl, amino, primary amino, secondary amino, corresponding ammonium groups and hydroxy, each being bonded directly or via a bridge group to the olefin group. The bridge groups may be —C(O)—, —C(O)—O-alkylene-, —C(O)—NH-alkylene-, —C(O)—O—$(C_2-C_6$alkylene-O$)_{1\ to\ 12}$—$C_2-C_6$alkylene-, —C(O)—NH—$(C_2-C_6$alkylene-O$)_{1\ to\ 12}$—$C_2-C_6$alkylene- or —O-alkylene-. Acidic hydrophilic groups, for example —C(O)OH, may also be present in the form of salts, for example in the form of alkali metal or alkaline earth metal salts.

The hydrophilic monomers (A) or (B) may correspond, for example, to formula I $$R_1R_2C=CR_3-Z \qquad (I)$$

wherein $R_1$, $R_2$ and $R_3$ are each independently of the other hydrogen or a hydrophobic substituent, and Z is a hydrophilic radical.

A hydrophobic substituent may be, for example, $C_1-C_{12}$alkyl, preferably $C_1-C_6$alkyl, $C_1-C_{12}$alkoxy, preferably $C_1-C_6$alkoxy, $C_1-C_{12}$haloalkyl, preferably $C_1-C_6$haloalkyl, phenyl, halophenyl, for example chlorophenyl, $C_1-C_4$alkylphenyl, $C_1-C_4$alkoxyphenyl, a carboxylic acid ester group having a total of from 2 to 20 carbon atoms, —CN, F or Cl.

In a preferred form, in formula I $R_1$ and $R_2$ are hydrogen and $R_3$ is hydrogen or methyl.

The hydrophilic radical may be, for example, —OH, —O—$(C_2-C_{12}$alkylene)—OH and preferably —O—$(C_2-C_6$alkylene)—OH, —C(O)—$NH_2$, —C(O)—NH—$(C_2-C_{12}$alkylene) —OH and preferably —C(O)—NH—$(C_2-C_6$alkylene)—OH, —C(O)—N—$(C_2-C_{12}$alkylene$)_2$—OH and preferably —C(O)—N—$(C_2-C_6$alkylene$)_2$—OH, —C(O)—NH—$C_1-C_{12}$alkyl and preferably —C(O)—NH—$C_1-C_6$alkyl, —C(O)—N—$(C_1-C_{12}$alkyl$)_2$ and preferably —C(O)—N—$(C_1-C_6$alkyl$)_2$, pyrrolidonyl, —C(O)—NH—$C_1-C_{12}$alkylene-$NH_2$ and preferably —C(O)—NH—$C_1-C_6$alkylene-$NH_2$, —C(O)—NH—$C_1-C_{12}$alkylene-NH—$C_1-C_6$alkyl and preferably —C(O)—NH—$C_2-C_6$alkylene-NH—$C_1-C_4$alkyl, —C(O)—NH—$C_1-C_{12}$alkylene-N—$(C_1-C_6$alkyl$)_2$ and preferably —C(O)—NH—$C_2-C_6$alkylene-N—$(C_1-C_4$alkyl$)_2$, or —C(O)—O—$(C_2-C_{12}$alkylene)—OH and preferably —C(O)—O—$(C_2-C_6$alkylene)—OH, or —C(O)—O—$(C_2-C_6$alkylene-O$)_{1\ to\ 12}$—$C_2-C_6$alkylene-OH or —C(O)—NH—$(C_2-C_6$alkylene-O$)_{1\ to\ 12}$—$C_2-C_6$alkylene-OH having the same or different alkylene —O— radicals which are preferably present from 1 to 6,especially from 1 to 4, times, and alkylene is preferably ethylene, 1,2- or 1,3-propylene or 1,4-butylene.

Some examples of those monomers A are vinyl alcohol, hydroxy-$C_2-C_6$alkylvinyl ethers, acrylamide, methacrylamide, methyl acrylamide, methyl methacrylamide, ethyl acrylamide, ethyl methacrylamide, n- or iso-propyl acrylamide, n- or iso-propyl methacrylamide, n-, iso- or tert-butyl acrylamide, n-, iso- or tert-butyl methacrylamide, dimethyl acrylamide, dimethyl methacrylamide, diethyl acrylamide, diethyl methacrylamide, di-n- or di-iso-propyl acrylamide, di-n- or di-iso-propyl methacrylamide, di-n-, di-iso- or di-tert-butyl acrylamide, di-n-, di-iso- or di-tert-butyl methacrylamide, pyrrolidone, hydroxyethyl acrylate and methacrylate, hydroxy-1,2-propyl acrylate and methacrylate, hydroxy-1,3-propyl acrylate and methacrylate, hydroxy-1,2-butyl acrylate and methacrylate, hydroxy-1,3-butyl acrylate and methacrylate, hydroxy-1,4-butyl acrylate and methacrylate, hydroxy-1,2-pentyl acrylate and methacrylate, hydroxy-1,3-pentyl acrylate and methacrylate, hydroxy-1,4-pentyl acrylate and methacrylate, hydroxy-1,5-pentyl acrylate and methacrylate, hydroxy-1,2-hexyl acrylate and methacrylate, hydroxy-1,3-hexyl acrylate and methacrylate, hydroxy-1,4-hexyl acrylate and methacrylate, hydroxy- 1,5-hexyl acrylate and methacrylate, hydroxyethyl acrylamide and methacrylamide, hydroxy-1,2-propyl acrylamide and methacrylamide, hydroxy-1,3-propyl acrylamide and methacrylamide, hydroxy-1,2-butyl acrylamide and methacrylamide, hydroxy-1,3-butyl acrylamide and methacrylamide, hydroxy- 1,4-butyl acrylamide and methacrylamide, hydroxy-1,2-pentyl acrylamide and methacrylamide, hydroxy-1,3-pentyl acrylamide and methacrylamide, hydroxy-1,4-pentyl acrylamide and methacrylamide, hydroxy-1,5-pentyl acrylamide and methacrylamide, hydroxy-1,2-hexyl acrylamide and methacrylamide, hydroxy-1,3-hexyl acrylamide and methacrylamide, hydroxy-1,4-hexyl acrylamide and methacrylamide, hydroxy-1,5-hexyl acrylamide and methacrylamide, hydroxy-1,6-hexyl acrylamide and methacrylamide, hydroxypolyoxyalkylene vinyl ethers, hydroxypolyoxyalkylene acrylate or methacrylate.

The component (b) polymer preferably comprises at least one identical monomer (A) of component (a) or a monomer (B) different from monomer (A), or a mixture of those monomers. In the case of a copolymer, the polymer comprises different monomers (A), or monomers (A) and monomers (B). Homopolymers are composed of monomers (A) or of monomers (B). In a preferred form of the composition according to the invention the component (b) polymer is composed of a monomer (A) selected from the same group of monomers (A) and is the same or different, the group being, for example, acrylates and/or methacrylates, acrylamides and/or methacrylamides, vinyl alcohols and/or hydroxyalkyl vinyl ethers, pyrrolidone and styrene. In an especially preferred form of the composition according to the invention the component (b) polymer is composed of the same monomer (A) as that used as monomer (A).

Some especially preferred combinations of hydrophilic monomers and polymers are vinyl pyrrolidone/pyrrolidone, acrylamide/polyacrylamide, acrylamide/polymethacrylamide, methacrylamide/polyacrylamide, ethyl acrylamide/polyethyl acrylamide, propyl acrylamide/polypropyl acrylamide, tert-butyl acrylamide/poly-tert-butyl acrylamide, tert-butyl acrylamide/polyacrylamide, tert-butyl acrylamide/polymethacrylamide, hydroxyalkyl vinyl ether/polyhydroxyalkyl vinyl ether, hydroxyethyl methacrylate/polyhydroxyethyl methacrylate, hydroxyethyl methacrylate/polyhydroxyethyl acrylate, hydroxy-n-propyl methacrylate/polyhydroxy-n-propyl methacrylate, hydroxy-isopropyl methacrylate/polyhydroxy-isopropyl methacrylate, hydroxy-n-butyl methacrylate/polyhydroxy-n-butyl methacrylate, hydroxy-n-pentyl methacrylate/polyhydroxy-n-pentyl methacrylate, hydroxy-n-hexyl methacrylate/polyhydroxy-n-hexyl methacrylate.

The hydrophobic monomers (A) or (B) may correspond, for example, to formula III

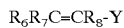

$$R_6R_7C=CR_8-Y \quad (III)$$

wherein $R_6$, $R_7$ and $R_8$ are each independently of the other hydrogen or a hydrophobic substituent, and Y is a hydrophobic radical.

The hydrophobic substituents may be, for example, $C_1-C_{12}$alkyl, preferably $C_1-C_6$alkyl, $C_1-C_{12}$alkoxy, preferably $C_1-C_6$alkoxy, $C_1C_{12}$haloalkyl, preferably $C_1-C_6$haloalkyl, phenyl, halophenyl, for example chlorophenyl, $C_1-C_4$alkylphenyl, $C_1-C_4$alkoxyphenyl, a carboxylic acid ester group having a total of from 2 to 20 carbon atoms, —CN, F or Cl.

The hydrophobic radical Y may be a radical as mentioned for $R_6$ to $R_8$. Preferred radicals Y are $C_1-C_6$alkyl, $C_1-C_6$alkoxy, phenyl, chlorophenyl, $C_1-C_4$alkylphenyl, $C_1-C_4$alkoxyphenyl, carboxylic acid ester groups having a total of from 2 to 10 carbon atoms, —CN and Cl.

In a preferred form, in formula III $R_6$ and $R_7$ are hydrogen and $R_8$ is hydrogen or methyl.

Some preferred combinations of hydrophobic monomers and polymers are styrene/polystyrene, methyl acrylate/polymethyl acrylate, methyl methacrylate/polymethyl methacrylate, vinyl ethyl ether/polyvinyl ethyl ether, acrylonitrile/polyacrylonitrile and acrylonitrile/polystyrene.

The component (b) polymer may have a mean molecular weight of from 1000 to 1 000 000 daltons, preferably from 10 000 to 500 000 daltons, determined in accordance with the gel permeation method using standard polymers of known molecular weight.

The indicator dye is preferably a fluorophore for the detection of changes in emissions, for example fluorescence.

The indicator dye may be a dye of formula II

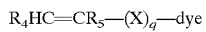

$$R_4HC=CR_5-(X)_q-dye \quad (II)$$

wherein $R_4$ is methyl and $R_5$ is hydrogen, or $R_5$ is methyl and $R_4$ is hydrogen, q is 0 or 1, X is a bridge group, and dye is the monovalent radical of a dye indicator.

In a preferred form, $R_4$ is hydrogen and $R_5$ is hydrogen or methyl.

In a different preferred form, q is 1.

The bridge group X may be, for example, —O—, —NH, —NH—$C_1-C_4$alkyl, —C(O)—O—, —C(O)—NH—, —C(O)—NH—$C_1-C_4$alkyl-, —NH—(CO)—O—, —O—C(O)—NH—, —C(O)—O—$C_2-C_{12}$alkylene-O—C(O)—, —C(O)—NH—$C_2-C_{12}$alkylene—O—C(O)—, —C(O)—O—$C_2-C_{12}$alkylene-NH—C(O)—, —C(O)—NH—$C_2-C_{12}$alkylene-NH—C(O)—, —C(O)—NH—$C_2-C_{12}$alkylene-C(O)—NH—, —NH—C(O)—O—$C_2-C_{12}$alkylene-O—C(O)—, —C(O)—O—$(C_2-C_6\text{alkylene-O})_{1 \text{ to } 12}$—, —C(O)—O—$(C_2-C_6\text{alkylene-O})_{1 \text{ to } 12}$—$C_2-C_6$alkylene-NH—, —C(O)—NH—$(C_2-C_6\text{alkylene-O})_{1 \text{ to } 12}$—$C_2-C_6$alkylene-NH—, —C(O)—NH—$(C_2-C_6\text{alkylene-O})_{1 \text{ to } 12}$—$CH_2$—C(O)—NH—.

Preferred bridge groups are —C(O)—NH—, —C(O)—O—$(CH_2CH_2$—$O)_{1 \text{ to } 6}$—, —C(O)—NH—$(CH_2CH_2$—$O)_{1 \text{ to } 6}$—$CH_2C(O)$—NH—, —C(O)—NH—$(C_2-C_6$alkylene-$O)_{1 \text{ to } 6}$—$C_2-C_6$alkylene-NH— and —C(O)—NH—$C_2-C_{12}$alkylene-C(O)—NH—.

The dye indicator may be a dye indicator that changes its absorption or emission under the action of a test sample and thus produces a measurable signal. Especially preferred are fluorescent dyes (fluorophores), for example those of the group of xanthenes and benzoxanthenes (for example fluorescein, halogenated fluoresceins, seminaphthofluoresceins, seminaphthorhodafluores, 2,3-benzfluorescein, 3,4-benzfluorescein, the isomers of benzrhodamine and substituted derivatives, the isomers of benzchromogene and substituted derivatives); acridines (for example acridine, 9-amino-6-chloroacridine); acridones (for example 7-hydroxyacridone, 7-hydroxybenzacridone); pyrenes (for example 8-hydroxypyrene-1,3,6-trisulfonic acid); coumarins (for example 7-hydroxycoumarin, 4-chloromethyl-7-hydroxycoumarin); conjugated cyanine dyes and metal complexes, for example platinum porphyrins. The fluorescent dyes are olefinically functionalised for bonding to a polymer.

Especially preferred fluorophores are 3- or 4-acryloylaminofluorescein and 3- or 4-methacryloylaminofluorescein.

A wide variety of absorption dyes for sensors is known. Examples are methyl violet, crystal violet, malachite green oxalate, methyl green, quinaldine red, 4-phenylazodiphenylamine, thymol blue (thymolsulfonephthalein), metacresol purple, orange IV, benzopurpurine 4B, N,N-dimethyl-p-(m-tolylazo)amine, bromophenol blue, congo red, methyl orange, bromocresol green, resazurin, 4-phenylazo-1-naphthylamine, ethyl red, lacmoid, alizarine red S, bromocresol purple, chlorophenol red, alizarine, bromothymol blue, brilliant yellow, phenol red, neutral red, cresol red, metacresol purple, thymol blue, o-cresolphthalein, p-naphtholbenzein, phenolphthalein, thymolphthalein, alizarine yellow R, curcumin, alizarine. The absorption dyes are olefinically functionalised for bonding to a polymer.

Suitable functional groups for bonding to a carbon atom of the olefinic group (directly or via a bridge group) are, for example, —OH, —$NH_2$, —NH—$C_1-C_4$alkyl, —C(O)OH, —C(O)Cl, —$SO_2Cl$, —C(O)—$NH_2$, —C(O)—NH—$CH_2CH_2$—OH, —C(O)—O—$CH_2CH_2$—OH, —C(O)—NH—$CH_2CH_2$—$NH_2$, —C(O)—O—$CH_2CH_2$—$NH_2$, —NH—C(O)—$CH_2OH$, —$CH_2I$, —$CH_2Br$, —$CH_2Cl$, —NCS, —NCO, —$N_3$ and succinyl esters. Vinyl or methylvinyl is suitable for direct bonding. The indicator dye may also be bonded directly or via a bridge group to the nitrogen atom of an unsubstituted or substituted maleinimidyl group.

Suitable cross-linking agents are, for example, acrylic or methacrylic acid esters or amides of polyols, preferably diols to tetrols, or polyamines, preferably diamines to tetramines. Aliphatic and cycloaliphatic diols and diamines are preferred. Such cross-linking agents are known and many are described in the literature. Some examples of polyols are alkylene diols, such as ethylene glycol, 1,3-propanediol, 1,4-butanediol, 1,6-hexanediol, diethylene glycol, polyalkylene diols of preferably $C_2$–$C_6$alkylene diols having especially from 3 to 100 alkylene diol units, for example polyethylene glycols, polypropylene glycols, polybutylene glycols and polyethylene-propylene glycols, 1,1,1-trihydroxymethyl-ethane or -propane, pentaerythritol and dipentaerythritol. Some examples of polyamines are ethylenediamine, 1,3-propanediamine, 1,4-butanediamine, 1,6-hexanediamine, diethylenetriamine and triethylenetetramine. Other known cross-linking agents are, for example, divinylbenzene and bis(dimethylmaleinimidyl)alkylenes, for example methylene or 1,2-ethylene-bis(dimethylmaleinimidyl).

Some examples are N,N'-methylene-bis-acrylic acid amide, N,N'-ethylene-bis-acrylic acid amide, N,N'-propylene-bis-acrylic acid amide, ethylene glycol bismethacrylate, propylene glycol bismethacrylate, butylene glycol bismethacrylate, hexylene glycol bismethacrylate and polyethylene glycol bismethacrylates of polyethylene glycols having mean molecular weights of from 200 to 3000.

The composition according to the invention comprises polymerisation initiators which can be activated either thermally or by the action of radiation. Examples of thermal initiators are radical formers, for example organic azo compounds, peroxo compounds and peroxodisulfates. Some examples are α,α'-azo-bisisobutyronitrile or ammonium peroxodisulfate. Examples of photoinitiators that can be activated by radiation, for example UV light, which can optionally be used together with sensitisers, are benzophenones, xanthones, thioxanthones, α-sec-aminoacetophenones and α-hydroxy-acetophenones.

The components of the composition according to the invention are known or can be prepared in accordance with known or analogous processes. Functionalised indicator dyes are known or can be prepared and derivatised with reagents that form bridge groups in accordance with known or analogous processes. Aminofluorescein acrylamide is commercially available. Rhodamines derivatised with carboxyalkyl groups are described, for example, by T. Werner et al. in Journal of Fluorescence, Vol. 2, No. 2, pages 93 to 98 (1992). The carboxy groups may, if desired, he functionally derivatised in known manner (amides, amines etc.). The composition according to the invention may comprise additives for improving processability, for example flow agents, viscosity-increasing or viscosity-reducing agents and solvents.

It is generally advantageous, however, to add a solvent or diluent or a mixture of solvents. Polar and, optionally, protic solvents are preferred. Examples of such solvents and diluents that may be mentioned are: water; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxy-diethyl ether, tetrahydrofuran or dioxane; ketones, such as acetone, methyl ethyl ketone or methyl isobutyl ketone; alcohols, such as methanol, ethanol, propanol, isopropanol, butanol, ethylene glycol or glycerol; amides, such as N,N-dimethylformamide, N,N-diethylformamide, N,N-dimethylacetamide, N-methylpyrrolidone or hexamethylphosphoric acid triamide; nitriles, such as acetonitrile or propionitrile; and sulfoxides, such as dimethyl sulfoxide. Preferred solvents are water, alkanols and N-dialkylated carboxylic acid amides.

The composition according to the invention is excellently suitable for the coating of carrier materials, especially carriers which may be transparent, in accordance with customary surface-coating methods, the layer being polymerised in a manner known per se after the coating and where appropriate after removal of a co-used solvent. The coated material is especially suitable for the manufacture of sensors. The composition according to the invention is excellently suitable for the manufacture of membranes for optical sensors.

The invention relates also to a method of coating carrier materials wherein the composition according to the invention is applied to at least one surface of the carrier material, where appropriate a solvent is removed, and the layer is polymerised.

For the purpose of improving adhesion the carrier materials may be treated beforehand with adhesion promoters. For the same purpose it is also possible to carry out plasma treatment of the carrier material in order to generate functional groups on the surface. The surface may also be provided with copolymerisable groups in order to achieve an especially high degree of adhesion. Known adhesion promoters for glass are, for example, triethoxy-glycidyloxysilane, 3-azidopropyl-triethoxysilane or 3-aminopropyl-triethoxysilane. The surfaces so treated can be further modified, for example with O-(N-succinimidyl)-6-(4'-azido-2'-nitrophenylamino)-hexanoate. It has proved especially advantageous to treat the surfaces with silanes of ethylenically unsaturated carboxylic acid esters, for example methacrylic acid 3-trimethoxysilyipropyl ester, because in the polymerisation the layer can be anchored covalently to the surface. Known coating techniques are, for example, spreading, immersion, knife application, spraying, casting, curtain casting or, especially, spin casting or spin coating respectively. It is especially advantageous that the coating itself can be effected with aqueous solutions and in this case too spin coating processes can be used.

The invention relates also to a carrier material wherein a layer of the composition according to the invention has been applied to at least one surface.

The invention relates also to a carrier material wherein a polymer layer of the composition according to the invention has been applied to at least one surface. The polymer layers are optically transparent and are therefore especially suitable for optical detection methods.

The invention relates also to an optical sensor wherein a polymer layer of the composition according to the invention has been applied to at least one surface. In this form of the invention there is preferably no proton-sensitive fluorophore for pH detection present in a hydrophilic polymer layer.

The invention relates also to the use of the sensors according to the invention for the optical determination of ions and gases (for example $O_2$ or $CO_2$ in blood). In this form of the invention there is preferably no proton-sensitive fluorophore for pH detection present in the hydrophilic polymer layer.

The invention relates also to a polymer from a composition according to the invention, preferably in the form of an unsupported film which can be used directly as an optical sensor. The polymers may be obtained, for example, by detaching the layers from the carrier material or by means of polymerisation in moulds.

The geometric shape of the carrier material may vary to a very great extent; for example, it may be in the form of fibres, cylinders, spheres, cuboids or cubes. Also possible are throughflow systems in which continuous measurements or successive measurements can be made. Planar sensors are preferred. The carrier material is preferably transparent. It may be, for example, inorganic glass or transparent plastics, such as polycarbonate, polyesters, polyamides or polyacrylates or polymethacrylates. In another preferred form the carrier material of the optical sensors is transparent and preferably consists of glass or a transparent polymer.

The planar sensor may have any desired external shape, for example it may be square, rectangular or round. It may have a surface area of from 0.01 to approximately 50 cm$^2$, advantageously from 0.02 to 10 cm$^2$. The measuring region of the sensor may have an area of, for example, less than 5 mm$^2$, preferably less than or equal to 2 mm$^2$. The measuring region can be identical with a fully coated surface of the sensor. Advantageously a coating provided on both sides but locally separated can be used.

The thickness of polymer layer (b) may be, for example, from 0.01 to 50 $\mu$m, preferably from 0.1 to 25 $\mu$m and especially from 0.1 to 10 $\mu$m.

The forms of the invention mentioned above are subject to the same preferences as those indicated for the composition according to the invention.

The polymerisation of the composition according to the invention can be carried out using thermal initiators at elevated temperature, for example from 40° to 200° C. and preferably from 50° to 150° C. The photopolymerisation can be carried out at room temperature. In that case an increase in temperature as mentioned earlier can be used to accelerate the reaction. The polymers may also be prepared by plasma polymerisation.

For the determination of cations and anions there are generally also incorporated ionophores which on contact with the analysis solution produce as a result of interaction with the indicator dye a change in the absorption or emission in the form of a measurable signal, thus allowing optical determination. As a rule in such systems, salts, such as tetraphenyl borate, and optionally buffers are also used. If the indicator dye is proton-sensitive, that sensitivity can be utilised directly for the determination of the pH value or indirectly in pH-altering reactions for the determination of ions (anions or metal cations). The determination of potassium is described, for example, by T. Werner et al. in Journal of Fluorescence, Vol. 2, No. 2, pages 93 to 98 (1992) and can be carried out analogously to that process. The pH determination using two sensors having different dependencies on the ionic strength of the measuring solution is described in DE-A-3 430 935 and can be carried out analogously using the sensors according to the invention. The radiation used for measurement may be selected from the UV range by way of the visible range to the near IR range (NIR range); the choice is substantially dependent upon the nature of the dye indicator.

The hydrophilic polymer membranes prepared according to the invention are especially suitable for the optical detection of the pH value in aqueous electrolyte solutions in the physiological range, for example in blood or blood serum, if a proton-sensitive fluorophore is present in the membrane.

The method for the independent, reversible, optical determination of the pH value and the ionic strength of an aqueous sample (electrolyte solution) with the aid of two different sensors in accordance with the fluorescence method can be carried out, for example, as follows: two optical sensors, which are each composed of polymers of different structure but each contain the same fluorescent dye and which each consist of a coated material according to the invention, are brought into contact with an aqueous test sample and irradiated with exciting light, the fluorescence is measured and the pH values and the ionic strengths are calculated from the measured fluorescence intensities with reference to calibration curves.

In detail, a procedure may be carried out in which, after calibration with samples of known ionic strength and known pH, the fluorescence intensity in contact with an electrolyte solution of unknown composition is measured and the separate contributions of the ionic strength and the pH to the measured fluorescence intensity are determined by calculation. The measurement data obtained from the calibrations are evaluated by calculation, for example using a pattern recognition algorithm. Using the calculation method the pH and the ionic strength can then be determined from the measurement data obtained. Both precalibration and direct calibration can be carried out.

The sensors are brought into contact with the calibration solutions or with the test samples. This can be done by hand (for example using pipettes) or with a suitable automatic throughflow system, the sensors being rigidly mounted in a flow cell. Such throughflow cells are known to the person skilled in the art and they can be simply adapted to the particular intended use.

As light sources for exciting the fluorescence it is possible to use UV lamps (for example mercury vapour lamps, halogen lamps), lasers, diode lasers and light-emitting diodes. It may be advantageous to use filters to filter out light of the wavelength at which the fluorescent dye has an absorption maximum. The fluorescent light emitted by the sensors can be collected, for example using a lens system, and then guided to a detector, for example a secondary electron multiplier or a photodiode. The lens system can be so arranged that the fluorescence radiation through the transparent carrier, over the edges of the carrier or through the analysis sample is measured. Advantageously the radiation is guided in a manner known per se via a dichroic mirror. The fluorescence of the sensors is preferably measured while in contact with the calibration or sample solutions.

An example of the procedure for the measuring method is described in the Examples.

The following Examples illustrate the invention.

A) PREPARATION EXAMPLES

Examples A1 to A9: Preparation of coated carriers (sensors)

Example A1:

Glass substrates (plates of 18 mm diameter) are first cleaned with 30% sodium hydroxide solution and then activated in 65% nitric acid. The activated plates are then silanised with methacrylic acid 3-trimethoxysilylpropyl ester. 150 $\mu$l of hydroxyethyl methacrylate, 5 mg of N,N-methylenebisacrylic acid amide, 2 mg of 4-acryloylaminofluorescein and 20 mg of ammonium peroxodisulfate are added to 4 ml of solution taken from a stock solution of 4 g of polyhydroxyethyl methacrylate in 60 ml of dimethylformamide. 50 $\mu$l of the resulting mixture are transferred by pipette to a plate lying on the head of a spin coater and the plate is spun for 30 seconds at a speed of 5000 revolutions per minute. For polymerisation the coated plates are then kept in an oven at 64° for 2 to 3 hours. Transparent substrates having a polymer layer of about 1 $\mu$m thickness are obtained. The polymer layer has good mechanical stability.

Example A2:

Glass substrates (plates of 18 mm diameter) are first cleaned with 30% sodium hydroxide solution and then activated in 65% nitric acid. The activated plates are then silanised with methacrylic acid 3-trimethoxysilylpropyl ester. 150 $\mu$l of hydroxyethyl methacrylate, 5 mg of N,N-methylenebisacrylic acid amide, 2 mg of 4-acryloylaminofluorescein and 10 mg of Irgacure 651® (photoinitiator, Ciba-Geigy AG) are added to 4 ml of solution taken from a stock solution of 4 g of polyhydroxyethyl methacrylate in 60 ml of dimethylformamide. 50 µl of the resulting mixture are transferred by pipette to a plate lying on the head of a spin coater and the plate is spun for 30 seconds at a speed of 5000 revolutions per minute. For polymerisation the coated plates are then irradiated with UV light (365 nm, 1300 µW/cm$^2$) for 10 to 20 minutes at room temperature. Transparent substrates having a polymer layer of about 1 µm thickness are obtained. The polymer layer has good mechanical stability.

Examples A3 to A7:

In a manner analogous to that described in Examples A1 and A2 it is also possible to prepare the other membranes listed in Table 1.

TABLE 1

| polymer[1] | mg | sol | monomer[2] | µl | mg dye[3] | mg cross-linking agent[4] | mg initiator |
|---|---|---|---|---|---|---|---|
| PVP | 600 | DMF | VP | 300 | 4 | 10 | 40[5] |
| PVP | 600 | DMF | VP | 300 | 4 | 10 | 20[6] |
| PAA | 800 | H$_2$O | AA | 150 | 2 | 5 | 20[5] |
| PHEMA | 270 | DMF | HEMA | 150 | 2 | 5 | 20[5] |
| PHEMA | 270 | DMF | HEMA | 150 | 2 | 5 | 10[6] |
| PHPMA | 1600 | DMF | HPMA | 300 | 4 | 10 | 40[5] |
| PHBA | 670 | DMF | HBA | 300 | 4 | 10 | 40[5] |

[1]PVP: polyvinylpyrrolidone, PAA: polyacrylamide, PHEMA: polyhydroxyethyl methacrylate, PHPMA: polyhydroxypropyl methacrylate, PHBA: polyhydroxybutyl acrylate
[2]VP: vinylpyrrolidone, AA: acrylamide, HEMA: hydroxyethyl methacrylate, HPMA: hydroxypropyl methacrylate, HBA: hydroxybutyl acrylate
[3]4-acryloylaminofluorescein
[4]N,N-methylenebisacrylic acid amide
[5]ammonium peroxodisulfate
[6]Irgacure ® 651
sol = solvent
DMF = dimethylformamide

B) APPLICATION EXAMPLES

Examples B1 to B8:

Two sensors are mounted one behind the other in two flow cells. The calibration solutions or sample solutions are metered and conveyed through the cells using pumps. The measuring arrangement is thermostatically controlled. The light of a halogen lamp (white light, excitation wavelength is 480 nm) is passed through an excitation filter, reflected on a dichroic mirror and focussed onto the planar sensors using lenses. The fluorescent light (at 520 nm) emitted by the sensors is collected using the same lens system and guided by the dichroic mirror via an emission filter to a photodiode. The fluorescence of the sensors is recorded while being acted upon by the calibration or sample solutions. The measurement data obtained from the calibrations are evaluated with a partial least squares pattern recognition algorithm; the calculation method is then capable of determining the pH and the ionic strength from the measurement data obtained from the sample.

The following Tables give the effects of the different membrane compositions on the properties of the embedded fluorescent dyes. Since the variation in the ionic strength alters not only the pK$_a$ of the dye but also the pH of the measuring solution, and the latter in turn influences the maximum fluorescence intensity of the dye, in order to measure the pH using the described sensor system it is necessary for the ionic strength dependency both of the pK$_a$ of the dye and of the pH of the calibration buffer solution to be known. Table 2 shows examples of fluorescent dyes, their pK$_a$, and the ionic strength dependency of the pK$_a$ and of the pH with different sensor membrane compositions. Sensors from the following Table having different ionic strength dependencies can be selected for pH determination.

TABLE 2

| polymer[1] | dye[2] | pK$_a$[3] | ionic strength dependency[4] | buffer curve displacement[5] |
|---|---|---|---|---|
| PVP | A | 6.3 | 0.02 | 0.02 |
| PAA | A | 6.4 | 0.13 | 0.10 |
| PHEMA | A | 7.0 | 0.28 | 0.25 |
| PHBA | A | 7.3 | 0.05 | 0.10 |
| PVP | B | 6.6 | 0.02 | 0.02 |
| PAA | B | 6.7 | 0.16 | 0.10 |
| PHEMA | B | 7.3 | 0.30 | 0.20 |
| PHPMA | B | 7.4 | 0.13 | 0.10 |

[1]for abbreviations see Table 1
[2]A: 4-acryloylaminofluorescein, B: 4-acryloylamino-4',5'-dimethylfluorescein
[3]at 0.1M ionic strength
[4]pK$_a$ displacement between the calibration curves in buffer solutions of 0.1M and 0.3M ionic strength
[5]pH displacement between the calibration curves in buffer solution of 0.1M and 0.3M ionic strength

What is claimed is:

1. A composition, comprising:
   (a) at least one olefinic monomer (A),
   (b) at least one polymer prepared from at least one olefinic monomer,
   (c) an indicator dye to the basic structure of which an olefinic polymerisable group is covalently bonded directly or via a bridge group,
   (d) at least one diolefinic cross-linking agent; and
   (e) an effective amount of a polymerisation initiator, characterized in that upon polymerisation of the composition a polymerisate is prepared in the form of an interpenetrating network.

2. A composition according to claim 1, wherein the monomers and polymers are hydrophilic and have a solubility in water of at least 1% by weight.

3. A composition according to claim 1, wherein the component (b) polymer is prepared from at least one monomer identical to (A), at least one monomer (B) that is different from (A), or a mixture of such monomers.

4. A composition according to claim 3, wherein the component (b) polymer is prepared predominantly or solely from monomer (A).

5. A composition according to claim 3, wherein the olefinic monomer(s) (A) and/or (B) are present in an amount of from 5 to 95% by weight, based on the composition.

6. A composition according to claim 1, wherein the component (b) polymers are present in an amount of from 95 to 5% by weight, based on the composition.

7. A composition according to claim 1, wherein the indicator dye is present in an amount of from 0.01 to 10% by weight.

8. A composition according to claim 1, wherein the polymerisation initiator is present in an amount of from 0.1 to 20% by weight.

9. A composition according to claim 1, wherein the cross-linking agent is present in an amount of from 0.1 to 30% by weight.

10. A composition according to claim 3, wherein the monomers (A) or (B) are selected from the group of olefins substituted by at least one hydrophilic radical.

11. A composition according to claim 10, wherein the hydrophilic radical(s) is/are selected from the group pyrrolidonyl, amino, primary amino, secondary amino, ammonium groups and hydroxy, each being bonded directly or via a bridge group to the olefin group.

12. A composition according to claim 11, wherein the bridge group is —C(O)—, —C(O)—O-alkylene-, —C(O)—NH-alkylene-, —C(O)—O—($C_2$-$C_6$alkylene-O)$_{1\ to\ 12}$—$C_2$-$C_6$alkylene-, —C(O)—NH—($C_2$-$C_6$alkylene-O)$_{1\ to\ 12}$—$C_2$-$C_6$alkylene- or —O-alkylene-.

13. A composition according to claim 10, wherein the monomers (A) or (B) correspond to formula I $$R_1R_2C=CR_3-Z \quad (I)$$

wherein $R_1$, $R_2$ and $R_3$ are each independently of the other hydrogen or a hydrophobic substituent, and Z is a hydrophilic radical.

14. A composition according to claim 13, wherein the hydrophobic substituent(s) is/are selected from $C_1$-$C_{12}$alkyl, $C_1$-$C_{12}$alkoxy, $C_1$-$C_{12}$haloalkyl, phenyl, halophenyl, $C_1$-$C_4$-alkylphenyl, $C_1$-$C_4$alkoxyphenyl, carboxylic acid ester groups having a total of from 2 to 20 carbon atoms, —CN, F and Cl.

15. A composition according to claim 13, wherein in formula I $R_1$ and $R_2$ are hydrogen and $R_3$ is hydrogen or methyl.

16. A composition according to claim 13, wherein the hydrophilic radical is —OH, —O—($C_2$-$C_{12}$alkylene)—OH, —C(O)—$NH_2$, —C(O)—NH—($C_2$-$C_{12}$alkylene)—OH, —C(O)—N—($C_2$-$C_{12}$alkylene)$_2$—OH, —C(O)—NH—$C_1$-$C_{12}$alkyl, —C(O)—N—($C_1$-$C_{12}$alkyl)$_2$, pyrrolidonyl, —C(O)—NH—$C_1$-$C_{12}$alkylene-$NH_2$, —C(O)—NH—$C_1$-$C_{12}$alkylene-NH—$C_1$-$C_6$alkyl, —C(O)—NH—$C_1$-$C_{12}$alkylene-N—($C_1$-$C_6$alkyl)$_2$, —C(O)—O—($C_2$-$C_{12}$alkylene)-OH, or —C(O)—O—($C_2$-$C_6$alkylene-O)$_{1\ to\ 12}$—$C_2$-$C_6$alkylene-OH or —C(O)—NH—($C_2$-$C_6$alkylene-O)$_{1\ to\ 12}$—$C_2$-$C_6$alkylene-OH having the same or different alkylene-O— radicals.

17. A composition according to claim 1, wherein the component (b) polymer is prepared from the same monomer (A) as that used as monomer (A).

18. A composition according to claim 1, wherein the component (b) polymer has a mean molecular weight of from 1000 to 1 000 000.

19. A composition according to claim 1, wherein the indicator dye is a dye of formula II $$R_4HC=CR_5-(X)_q-dye \quad (II)$$

wherein
$R_4$ is methyl and $R_5$ is hydrogen, or
$R_5$ is methyl and $R_4$ is hydrogen,
q is 0 or 1,
X is a bridge group, and
dye is the monovalent radical of a dye indicator.

20. A composition according to claim 19, wherein $R_4$ is hydrogen and $R_5$ is hydrogen or methyl.

21. A composition according to claim 19, wherein q is 1.

22. A composition according to claim 19, wherein the bridge group X is —O—, —NH, —NH—$C_1$-$C_4$alkyl-, -C(O)-O-, -C(O)-NH-, -C(O)—NH—$C_1$-$C_4$alkyl-, —NH—(CO)—O—, —O—C(O)—NH—, —C(O)—O— $C_2$-$C_{12}$alkylene-O—C(O)—, —C(O)—NH— $C_2$-$C_2$-$C_{12}$alkylene-O—C(O)—, —C(O)—O— $C_2$-$C_{12}$alkylene-NH—C(O)—, —C(O)—NH— $C_2$-$C_{12}$alkylene-NH—C(O)—, —C(O)—NH— $C_2$-$C_{12}$alkylene-C(O)—NH—, —NH—C(O)—O— $C_2$-$C_{12}$alkylene-O—C(O)—, —C(O)—O— ($C_2$-$C_6$alkylene-O)$_{1\ to\ 12}$—, —C(O)—O—($C_2$-$C_6$alkylene-O)$_{1\ to\ 12}$—$C_2$-$C_6$alkylene-NH—, —C(O)—NH—($C_2$-$C_6$alkylene-O)$_{1\ to\ 12}$—$C_2$-$C_6$alkylene-NH— or —C(O)—NH—(($C_2$-$C_6$alkylene-O)$_{1\ to\ 12}$—$CH_2$—C(O)—NH—.

23. A composition according to claim 1, wherein the cross-linking agent is selected from the group consisting of acrylic and methacrylic acid esters and amides of polyols and polyamines, divinyl benzene and bis(dimethylmaleinimidyl)alkylenes.

24. A composition according to claim 1, wherein the polymerisation initiator is an organic azo compound, peroxo compound, peroxodisulfate or a photoinitiator that can be activated by radiation.

25. A composition according to claim 1, which comprises a solvent.

26. A composition according to claim 3, wherein the hydrophobic monomers (A) or (B) correspond to formula I $$R_1R_2C=CR_3-Y \quad (III)$$

wherein $R_1$, $R_2$ and $R_3$ are each independently of the other hydrogen or a hydrophobic substituent, and Y is a hydrophobic radical.

27. A composition according to claim 26, wherein the hydrophobic substituent(s) is/are selected from $C_1$-$C_{12}$alkyl, $C_1$-$C_{12}$alkoxy, $C_1$-$C_{12}$haloalkyl, phenyl, halophenyl, $C_1$-$C_4$-alkylphenyl, $C_1$$C_4$alkoxyphenyl, carboxylic acid ester groups having a total of from 2 to 20 carbon atoms, —CN, F and Cl.

28. A composition according to claim 26, wherein in formula III $R_1$ and $R_2$ are hydrogen and $R_3$ is hydrogen or methyl.

29. A composition according to claim 26, wherein in formula III Y is $C_1$-$C_6$alkyl, $C_1$-$C_6$-alkoxy, phenyl, chlorophenyl, $C_1$-$C_4$alkylphenyl, $C_1$-$C_4$alkoxyphenyl, a carboxylic acid ester group having a total of from 2 to 10 carbon atoms, —CN or —Cl.

30. A carrier material, comprising: a layer of the composition according to claim 1 applied to at least one surface thereof, wherein the carrier material is suitable for use in the manufacture of optical sensors.

31. A carrier material, comprising: a layer of a polymerisate prepared from the composition according to claim 1 applied to at least one surface thereof, wherein the polymerisate is in the form of an interpenetrating network.

32. A carrier material according to claim 31 that is planar.

33. A carrier material according to claim 31 that is transparent.

34. A carrier material according to claim 31 that consists of a glass or a transparent polymer.

35. A carrier material according to claim 31, wherein the polymerisate layer has a thickness of from 0.01 to 50 µm.

36. An optical sensor, comprising: a layer of a polymerisate prepared from the composition according to claim 1 applied to at least one surface thereof, wherein the polymerisate is in the form of an interpenetrating network.

37. A method for the optical determination of ions or gases in a solution or blood, comprising:
contacting the solution or blood with an optical sensor comprising a polymerisate prepared from the composition according to claim 1, under conditions effective to cause a change in absorption or emission in the form of a measurable signal,
measuring the measurable signal; and
determining the presence and/or ionic strength of the ions or gases in the solution or blood by comparing the measurable signal to calibrated standards.

38. A polymerisate prepared from a composition according to claim 1, wherein the polymerisate is in the form of an unsupported film.

39. A composition according to claim 1 wherein the polymerisate is suitable for use in optical sensors.

40. A carrier material according to claim 31 wherein the polymerisate is suitable for use in optical sensors.

41. A polymerisate according to claim 38 wherein the unsupported film is suitable for use in optical sensors.

42. A transparent membrane, comprising:
a polymerisate of
- (a) at least one olefinic monomer (A),
- (b) at least one polymer prepared from at least one olefinic monomer,
- (c) an indicator dye to the basic structure of which an olefinic polymerisable group is covalently bonded directly or via a bridge group,
- (d) at least one diolefinic cross-linking agent; and
- (e) an effective amount of a polymerisation initiator, wherein the polymerisate is in the form of an interpenetrating network.

43. A transparent membrane according to claim 42 wherein the polymerisate is suitable for use in optical sensors.

* * * * *